US012760127B2

(12) United States Patent
Chan

(10) Patent No.: US 12,760,127 B2

(45) Date of Patent: Oct. 13, 2026

(54) ***AURICULARIA AURICULA* POLYSACCHARIDE, ITS APPLICATION AND PREPARATION METHOD THEREOF**

(71) Applicant: BEIJING BEIQING BOYU INFORMATION TECHNOLOGY RESEARCH CO. LTD, Beijing (CN)

(72) Inventor: Sun Sun Chan, mid Level (HK)

(73) Assignee: BEIJING BEIQING BOYU INFORMATION TECHNOLOGY RESEARCH CO. LTD, Beijing (CN)

( * ) Notice: Subject to any disclaimer, the term of this patent is extended or adjusted under 35 U.S.C. 154(b) by 0 days.

(21) Appl. No.: 18/015,393

(22) PCT Filed: Sep. 7, 2022

(86) PCT No.: PCT/CN2022/117433

§ 371 (c)(1),
(2) Date: Jan. 10, 2023

(87) PCT Pub. No.: WO2024/045207

PCT Pub. Date: Mar. 7, 2024

(65) Prior Publication Data

US 2025/0223381 A1 Jul. 10, 2025

(30) Foreign Application Priority Data

Aug. 31, 2022 (CN) ........................ 202211060080.0

(51) Int. Cl.

| | |
|---|---|
| ***C08B 37/00*** | (2006.01) |
| ***A61K 31/715*** | (2006.01) |
| ***A61P 3/06*** | (2006.01) |
| ***C12P 19/04*** | (2006.01) |
| ***C12P 19/20*** | (2006.01) |

(52) U.S. Cl.

CPC ........ *C08B 37/0003* (2013.01); *A61K 31/715* (2013.01); *A61P 3/06* (2018.01); *C12P 19/04* (2013.01); *C12P 19/20* (2013.01)

(58) Field of Classification Search

None

See application file for complete search history.

(56) References Cited

U.S. PATENT DOCUMENTS 7,029,883 B2 * 4/2006 Chan ...................... A61K 36/07
536/123

FOREIGN PATENT DOCUMENTS

| | | | | |
|---|---|---|---|---|
| CN | 102321186 | * | 1/2012 | |
| CN | 107177007 | * | 9/2017 | ........... C08B 37/000 |
| CN | 11010621 | * | 5/2019 | |
| CN | 111909285 | * | 11/2020 | |
| CN | 113549161 | * | 10/2021 | ........... C08B 37/000 |
| JP | WO 2006112036 | * | 10/2006 | |

OTHER PUBLICATIONS

Machine Transalation of CN 110106216 A, 7 pages (Year: 2019).*

* cited by examiner

*Primary Examiner* — Thane Underdahl

(74) *Attorney, Agent, or Firm* — Bayramoglu Law Offices LLC

(57) ABSTRACT

The invention provides an *Auricularia auricula* polysaccharide, its application and preparation method thereof, which belong to the technical field of improving polysaccharide. After being degreased, the *Auricularia auricula* is subjected to preliminary enzymolysis under the effect of helicase, is further subjected to deep enzymolysis under the effect of complex enzyme through synergetic ultrasound-assisted degradation and extraction with H2O2, and is subjected to mixed fermentation by *Lactobacillus bulgaricus, Streptococcus thermophilus* and *Bifidobacterium longum*, the obtained fermented *Auricularia auricula* polysaccharide is subjected to a phosphorylation reaction under the effect of a phosphorylation reagent, and after further deproteinization and decolorization, the obtained fermented *Auricularia auricula* polysaccharide is chelated with zinc salt to obtain a polysaccharide-zinc compound, and the amount of the extracted *Auricularia auricula* polysaccharide is improved. The finished product of the invention has the effects of reducing blood sugar and blood fat, regulating total cholesterol and effectively improving HDL cholesterol.

12 Claims, 2 Drawing Sheets

*AURICULARIA AURICULA* POLYSACCHARIDE, ITS APPLICATION AND PREPARATION METHOD THEREOF

TECHNICAL FIELD

The invention relates to the technical field of polysaccharide, in particular to an *Auricularia auricula* polysaccharide, its application and preparation method thereof.

BACKGROUND

*Auricularia auricula* belongs to Basidiomycetes, Auriculariales, Auriculariaceae, *Auricularia. Auricularia auricula* is a precious medicinal and edible colloidal fungus in China, which tastes delicious, has rich nutrition, and has the effects of nourishing the blood and retaining youthful looks, and eliminating disease and prolonging life. Traditional Chinese medicine believes that *Auricularia auricula* is sweet and neutral in property and flavor, has the effects of clearing lung and moistening intestines, nourishing yin and supplementing blood, promoting blood circulation and removing blood stasis, improving eyesight and nourishing stomach, and is effective for metrorrhagia and metrostaxis, hemorrhoids, bloody dysentery, anemia and constipation. Modern pharmacological studies have shown that the biological activity of *Auricularia auricula* mainly comes from its polysaccharides. As a "biological response modifier", the *Auricularia auricula* polysaccharide has anti-coagulation, anti-tumor, anti-inflammatory and other cytoprotective effects, and also has various biological functions of reducing blood lipids, blood sugar, blood viscosity, and cholesterol, as well as resisting diabetes, aging, radiation and the like.

The *Auricularia auricula* polysaccharide is also accepted as a natural health product. The traditional extraction techniques include a hot water extraction method and a dilute lye extraction method. Wherein, the hot water extraction method is a traditional method of extracting fungal polysaccharides, which is commonly used at home and abroad. However, an extractant distilled water required in this method is economical and easy to obtain, but it needs to be extracted for multiple time, and the yield is still very low, which is time-consuming and material-consuming. The dilute lye extraction method uses distilled water and 1 mol/L NaOH solution as extractants respectively, and extracts for 3 hours at 80 deg C., and the polysaccharide content by using the distilled water as the extractants is 1.28%, while the polysaccharide content by using the 1 mol/L NaOH solution as the extractants is 3.52%, and the polysaccharide content of the latter is higher than that of the former by about 3 times, time can be saved, and consumption of raw materials and reagents is reduced. However, there is still a defect of low extraction efficiency.

In recent years, people adopt an enzymolysis extraction method, an ultrasonic extraction method and a microwave-assisted extraction method to realize the extraction of the *Auricularia auricula* polysaccharide.

Enzymatic extraction is a combination of enzyme and hot water extraction. The enzymes are mostly pectinase, cellulase and neutral protease. This method has the advantages of mild conditions, easy removal of impurities and high yield. Patent CN107177007B discloses a preparation method of an *Auricularia auricula* polysaccharide.

An ultrasonic extraction method utilizes the high-frequency oscillation, high acceleration, strong "cavitation effect" and stirring effect generated by the ultrasonic wave to accelerate the effective bioactive ingredients to enter the solvent, thereby improving the extraction rate, shortening the extraction time, saving the solvent, and extracting at low temperature, which is beneficial to the protection of the effective ingredients. Patent application CN106496344A discloses an organic *Auricularia auricula* polysaccharide and a preparation method of its particles.

Microwave-assisted extraction has the advantages of simple equipment, wide application, high extraction rate, solvent saving, time saving, energy saving, no noise and pollution, and the like. It is a promising new assisted extraction process to enhance solid-liquid extraction process by microwave. A method for microwave-assisted extraction of *Auricularia auricula* polysaccharide is disclosed in patent application CN105367680A.

However, the above extraction methods of *Auricularia auricula* polysaccharides can effectively improve the extraction rate of polysaccharides, but are either time-consuming, low yield, or high cost, which cannot meet the market demand. In addition, due to poor solubility of *Auricularia auricula* polysaccharide, the further research and application in the development of food and medicine are greatly limited. At the same time, how to ensure the maximum retention of its activity in the process of extraction and application of *Auricularia auricula* polysaccharide is also the main factor that should be considered.

SUMMARY OF THE INVENTION

The invention aims to provide an *Auricularia auricula* polysaccharide and its application and preparation method thereof. The preparation method is simple and high in extraction efficiency; the prepared *Auricularia auricula* polysaccharide is high in purity, good in solubility, easy to absorb and good in physiological activity, not only has good effects of resisting oxidation, resisting inflammation, resisting aging, reducing blood sugar and the like, but also has the effects of reducing blood fat, regulating total cholesterol and effectively improving HDL cholesterol, and has wide application prospect.

The technical scheme of the invention is realized as follows:

the invention provides a preparation method of the *Auricularia auricula* polysaccharide, which comprises the following steps: degreasing *Auricularia auricula*, carrying out preliminary enzymolysis under the action of snailase, further carrying out synergetic ultrasound-assisted degradation and extraction with $H_2O_2$, carrying out secondary enzymolysis under the action of complex enzyme, then carrying out mixed fermentation of *Lactobacillus bulgaricus, Streptococcus thermophilus* and *Bifidobacterium longum*, the obtained fermented *Auricularia auricula* polysaccharide is subjected to a phosphorylation reaction under the action of a phosphorylation reagent, and after further deproteinization and decolorization, the obtained fermented *Auricularia auricula* polysaccharide is chelated with zinc salt to obtain a polysaccharide-zinc compound, namely the *Auricularia auricula* polysaccharide.

As a further improvement of the invention, the method comprises the following steps:

S1. Degreasing: drying and crushing the *Auricularia auricula*, and then degreasing the *Auricularia auricula* by a supercritical fluid extraction process to obtain the degreased *Auricularia auricula;*

S2. Preliminary enzymolysis: adding the degreased *Auricularia auricula* in the step S1 into water, adding the snailase, performing enzymolysis, deactivating enzyme, concentrating and drying to obtain a preliminary enzymolysis product;

S3. extraction under ultrasound in combination with $H_2O_2$: adding the preliminary enzymolysis product prepared in the step S2 into an $H_2O_2$ solution, carrying out ultrasonic treatment, adding sodium bisulfite to remove $H_2O_2$, carrying out alcohol precipitation, centrifuging and drying to obtain an *Auricularia auricula* raw sugar extract;

S4. secondary enzymolysis: dissolving the raw sugar extract prepared in the step S3 in water, adding complex enzyme for enzymolysis, and deactivating the enzyme to obtain a secondary enzymolysis extract;

S5. Strains activating: respectively streaking the *Lactobacillus bulgaricus*, the *Streptococcus thermophilus* and the *Bifidobacterium longum* in a Gauze's medium, and carrying out activation culture to obtain strain seed liquid;

S6. Fermentation: inoculating the strain seed liquid prepared in the step S5 into the secondary enzymolysis extract prepared in the step S4, and carrying out the steps of fermentation culture, concentration, alcohol precipitation and centrifugation to obtain the fermented *Auricularia auricula* polysaccharide;

S7. Phosphorylation: adding the fermented polysaccharide prepared in the step S6 into water, adding sodium sulfate and a phosphorylation reagent, adjusting the pH value to 8.8-9.2, performing the heating reaction, dialyzing, and concentrating to obtain a phosphorylated *Auricularia auricula* polysaccharide solution;

S8. Deproteinization: adding the phosphorylated *Auricularia auricula* polysaccharide solution obtained in the step S7 into the Sevage reagent, stirring for the reaction, centrifuging to remove denatured protein precipitate, repeating the steps for 1-3 times, merging the liquids, and removing the solvent under reduced pressure to obtain the deproteinized *Auricularia auricula* polysaccharide;

S9. Decolorization: adding activated carbon and the deproteinized *Auricularia auricula* polysaccharide prepared in the step S8 into water, stirring for adsorption, filtering, performing alcohol precipitation, and centrifuging to obtain the refined *Auricularia auricula* polysaccharide;

S10. Zinc chelating: dissolving the refined *Auricularia auricula* polysaccharide prepared in step S9 and trisodium citrate in water, adding zinc salt, adjusting a pH value of the solution to 7.2-7.5, performing the heating and stirring reaction, filtering, performing alcohol precipitation, centrifuging, collecting solid, and freeze-drying to obtain the *Auricularia auricula* polysaccharide.

As a further improvement of the present invention, conditions of the supercritical fluid extraction process in step S1 are that a flow rate of $CO_2$ is 7-12 L/h, a pressure of an extraction kettle is 12-25 MPa, a temperature is 45-60 deg C., and an extraction time is 1-2 h; a mass ratio of the degreased *Auricularia auricula* to the snailase is in a range of 100:5 to 100:3, a temperature of the enzymolysis is 40-50 deg C., and a time of the enzymolysis is 1-2 h; in the step S3, a concentration of $H_2O_2$ in a $H_2O_2$ solution is 2-5 wt %; a power of the ultrasonic treatment is 1500-2000 W, and a time of the treatment is 30-50 min; in the step S4, the complex enzyme is selected from at least two of β-glucanase, saccharifying enzyme, cellulase, pectinase, α-amylase and α-glucosidase; a mass ratio of the raw sugar extract to the complex enzyme is in a range of 100:7 to 100:5, a temperature of the enzymolysis is 40-45 deg C., and a time of the enzymolysis is 3-5 h.

As a further improvement of the present invention, the complex enzyme is a compound mixture of β-glucanase and α-glucosidase at a mass ratio of 3:1 to 5:1.

As a further improvement of the present invention, an activation culture condition in the step S5 is the low-oxygen condition, a temperature is 40-45 deg C., a time is 18-24 h, and a bacterial content of the strain seed liquid is $10^8$-$10^9$ cfu/mL; in the step S6, inoculum sizes of *Lactobacillus bulgaricus, Streptococcus thermophilus* and *Bifidobacterium longum* are respectively 3-5%, 1-3% and 1-2%; a fermentation culture condition is under the low-oxygen condition, a temperature is 40-45 deg C., and a time is 36-48 h; a low-oxygen condition is as follow: that a content of $O_2$ is 5 to 7%, the content of $CO_2$ is 5 to 10%, and the remanent is nitrogen, wherein % is the volume percentage content.

As a further improvement of the present invention, in the step S7, the phosphorylation reagent is selected from at least two of polyphosphoric acid, sodium tripolyphosphate, sodium trimetaphosphate, pyrophosphoric acid, and phosphorus pentoxide; a mass ratio of the fermented polysaccharide, sodium sulfate, the phosphorylation reagent, and water is 10: 30-50:2-4:100; a temperature of the heating reaction is 70-90 deg C., a time is 3-5 h, a dialysis bag used for the dialyzing has a pore size of 5000-15000 Da (Dalton), and the time is 24-48 h; in the step S8, a mass ratio of the phosphorylated *Auricularia auricula* polysaccharide solution to the Sevage reagent is in a range of 1:7 to 1:3; a stirring reaction time is 20-30 min; in the step S9, a mass ratio of the deproteinized *Auricularia auricula* polysaccharide to the activated carbon is in a range of 100:15 to 100:12; a stirring adsorption time is 30-50 min; in the step S10, a mass ratio of the *Auricularia auricula* polysaccharide to the trisodium citrate to the zinc salt is 100: 5-12:22-27; the temperature of the heating and stirring reaction is 45-55 deg C., a time is 1-2 h, and a stirring speed is 300-500 r/min; and the zinc salt is selected from at least one of zinc chloride, zinc sulfate and zinc nitrate.

As a further improvement of the invention, the phosphorylation reagent is a mixture of sodium tripolyphosphate, sodium trimetaphosphate and pyrophosphoric acid, and the mass ratio is 3-7:2:0.2-0.4.

As a further improvement of the invention, the method comprises the following steps:

S1. Degreasing: drying and crushing the *Auricularia auricula*, and then degreasing the *Auricularia auricula* by a supercritical fluid extraction process to obtain the degreased *Auricularia auricula*; wherein conditions of the supercritical fluid extraction process are as follows: a flow rate of $CO_2$ is 7-12 L/h, a pressure of the extraction kettle is 12-25 MPa, a temperature is 45-60 deg C., and an extraction time is 1-2 h;

S2. Preliminary enzymolysis: adding 100 parts by weight of degreased *Auricularia auricula* in the step S1 into 200 parts by weight of water, adding 3-5 parts by weight of the snailase, carrying out enzymolysis at 40-50 deg C. for 1-2 hours, deactivating enzyme at 100-110 deg C. for 10-15 min, concentrating an organic film to ⅓-¼ of the original volume, and drying to obtain a preliminary enzymolysis product;

S3. extraction under ultrasound in combination with $H_2O_2$: adding 100 parts by weight of the preliminary enzymolysis product prepared in the step S2 into 100 parts by weight of 2-5 wt % $H_2O_2$ solution, performing ultrasonic treatment for 30-50 min at 1500-2000 W, adding 7-12 parts by weight sodium bisulfite to remove $H_2O_2$, precipitating with alcohol, centrifuging, drying, and obtaining the *Auricularia auricula* raw sugar extract;

S4. secondary enzymolysis: dissolving 100 parts by weight of the raw sugar extract prepared in the step S3 in 100 parts by weight of water, adding 5-7 parts by mass of complex enzyme, carrying out enzymolysis at 40-45 deg C. for 3-5 h, and deactivating the enzyme at 100-110 deg C. for 10-15 min to obtain the secondary enzymolysis extract; wherein the complex enzyme is a compound mixture of β-glucanase and α-glucosidase at a mass ratio of 3:1 to 5:1;

S5. Strains activating: respectively streaking *Lactobacillus bulgaricus, Streptococcus thermophilus* and *Bifidobacterium longum* in a Gauze's medium, activating and culturing at 40-45 deg C. for 18-24 h under a low-oxygen condition to obtain the strain seed liquid with the bacteria content of $10^8$-$10^9$ cfu/mL;

S6. Fermentation: inoculating the strain seed liquid prepared in the step S5 into the secondary enzymolysis extract prepared in the step S4, wherein the inoculum sizes of *Lactobacillus bulgaricus, Streptococcus thermophilus* and *Bifidobacterium longum* are respectively 3-5%, 1-3% and 1-2%, fermenting and culturing at 40-45 deg C. for 36-48 h under the low-oxygen condition, concentrating, performing alcohol precipitation, and centrifuging to obtain the fermented *Auricularia auricula* polysaccharide; wherein low-oxygen condition is as follow: a content of $O_2$ is 5% to 7%, the content of $CO_2$ is 5% to 10%, and the remanent is nitrogen, wherein % is the volume percentage content;

S7. Phosphorylation: adding 10 parts by weight of the fermented polysaccharide prepared in the step S6 into 100 parts by weight of water, adding 30-50 parts by weight of sodium sulfate and 2-4 parts by weight of the phosphorylation reagent, adjusting the pH value to 8.8-9.2, heating at 70-90 deg C. to react for 3-5 h, dialyzing for 24-48 h by using a dialysis bag with the pore size of 5000-15000 Da, concentrating an organic membrane to ⅓-¼ of the original volume to obtain phosphorylated *Auricularia auricula* polysaccharide solution; wherein the phosphorylation reagent is a mixture of sodium tripolyphosphate, sodium trimetaphosphate and pyrophosphoric acid with the mass ratio of 3-7:2:0.2-0.4;

S8. Deproteinization: adding 10 parts by weight of the phosphorylated *Auricularia auricula* polysaccharide solution obtained in the step S7 into 30-70 parts by weight of the Sevage reagent, stirring for the reaction for 20-30 min, centrifuging to remove denatured protein precipitate, repeating for 1-3 times, merging the liquids, and removing the solvent under reduced pressure to obtain the deproteinized *Auricularia auricula* polysaccharide;

S9. Decolorization: adding 12-15 parts by weight of activated carbon and 100 parts by weight of the deproteinized *Auricularia auricula* polysaccharide prepared in the step S8 into 200 parts by weight of water, stirring for adsorption for 30-50 min, filtering, performing alcohol precipitation, and centrifuging to obtain the refined *Auricularia auricula* polysaccharide;

S10. Zinc chelating: dissolving 100 parts by weight of the refined *Auricularia auricula* polysaccharide prepared in step S9 and 5-12 parts by weight of trisodium citrate in 200 parts by weight of water, adding 22-27 parts by weight of zinc salt, adjusting the pH value of the solution to 7.2-7.5, heating to 45-55 deg C. and stirring for the reaction at 300-500 r/min for 1-2 h, filtering, performing alcohol precipitation, centrifuging, collecting solid, and freeze-drying to obtain the *Auricularia auricula* polysaccharide; wherein the alcohol precipitation method comprises the following steps of: adding absolute ethyl alcohol until the ethanol content in the system is 75-85%, and precipitating for 12-24 h.

The invention further protects the *Auricularia auricula* polysaccharide prepared by the preparation method.

The invention further protects the application of the *Auricularia auricula* polysaccharide in preparing products for reducing blood fat, regulating total cholesterol and effectively improving HDL cholesterol. The method has the following beneficial effects that the degreased *Auricularia auricula* after degreasing treatment is subjected to enzymolysis by using the snailase, the degreased *Auricularia auricula* contains a large amount of mixed enzymes with biological activities, such as cellulase, hemicellulase, pectinase, alpha amylase, seminase, sucrase, galactanase, proteolytic enzyme, amino acid transferase and the like, and under the enzymolysis action of the snailase, it is helpful to break the cell wall of *Auricularia auricula* and release the active substance polysaccharide in its cells better. Further, a preliminary enzymolysis product after snailase enzymolysis is subjected to extraction under ultrasound in combination with $H_2O_2$, a large amount of cell walls of the preliminary enzymolysis product are broken at this time, intracellular polysaccharide is dissolved out, $H_2O_2$ is a strong oxidant and can be used as an oxidant to perform an oxidative degradation reaction on organic compounds, but the oxidative degradation efficiency of $H_2O_2$ alone is low, and after ultrasound-assisted treatment, high quantum yield of a hydroxyl group can be generated. Ultrasonic wave can reduce the activation energy of the reaction, thus significantly increase the degradation rate and shorten the reaction time. The ultrasonic wave can promote the dissociation of $H_2O_2$, and $H_2O_2$ as a synergistic measure can effectively improve the degradation rate. The ultrasonic wave generates high-frequency physical vibration, reduces the cavitation effect caused by the internal pressure of an extraction system, and rapidly further damages the cell walls of a extract, so that more than 90% of cell walls are broken, the particle diffusion strength of active substances of the extract is increased, the friction and collision among particles are promoted to rapidly generate heat, the cell walls are damaged, the extraction time is obviously shortened, and the extraction efficiency is improved.

The enzymolysis of polysaccharide is mainly realized by changing the molecular weight, molecular structure, solubility and substituents of polysaccharides, and the enzymolysis is mainly realized by changing the type, quantity and physical and chemical properties of polysaccharides, and enhancing the biological activity. The *Auricularia auricula* polysaccharide is mainly composed of water-soluble β-D-glucan, water-insoluble β-D-glucan and two kinds of acidic heteropolysaccharides, and both of water-soluble β-D-glucan and water-insoluble β-D-glucan are connected by β-1,3-glycosidic bond. The β-glucanase can degrade the β-1,3-glycosidic bond and β-1,4-glycosidic bond efficiently, and make polysaccharide modified and solubilized. α-glucosidase has the dual functions of hydrolysis and transglycosidation, hydrolysis can make the non-reducing end of α-glucoside, oligosaccharide and glucan cut the α-1,4 glycosidic bond and release glucose; transglycosidation can transfer free glucose residues to another glucose or maltose substrate by α-1,6 glycosidic bond, thus obtaining non-fermentable isomaltooligosaccharide, the digestibility of polysaccharide products can be improved and the sweetness is reduced; under the synergistic effect of the β-glucanase and the α-glucosidase, the molecular weight of the *Auricularia* auricular polysaccharide can be reduced from high molecular weight to low molecular weight, the biological activity of the *Auricularia* auricular polysaccharide can be improved, and the low molecular weight polysaccharide is more easily absorbed by a human body.

*Lactobacillus bulgaricus*, a facultative anaerobe, can ferment glucose, fructose and lactose, but cannot utilize sucrose. *Streptococcus thermophilus*, the facultative anaerobic, ferments lactose, and does not ferment inulin and mannitol. *Bifidobacterium longum*, the facultative anaerobic, can utilize lactose, ribose, raffinose, xylose, mannose, fructose, galactose, sucrose, maltose, melibiose, and the like. *Streptococcus thermophilus, Bifidobacterium longum* and *Lactobacillus bulgaricus* are mixed for fermentation culture, which is better than separate fermentation culture, because *Lactobacillus bulgaricus* and *Bifidobacterium longum* are decomposed to provide lactic acid, amino acids and the like, which provide nutrients for the growth of *Streptococcus thermophilus*, and formic acid, short-chain fatty acids, folic acid and the like produced by *Streptococcus* thermophile, can promote the growth of the *Lactobacillus bulgaricus* and the *Bifidobacterium longum*; in the initial fermentation stage of the *Streptococcus thermophilus*, the acid production is fast, when the pH is reduced to about 6.2-6.7, the *Bifidobacterium longum* is promoted to proliferate in a large amount, and a large amount of small molecular acid is further produced; when the pH is continuously reduced to about 4, the *Lactobacillus bulgaricus* proliferates in a large amount, and a large number of lactic acid and amino acid are produced; on the contrary, the growth of the *streptococcus acidophilus* and the *Bifidobacterium longum* is promoted, and the three complement each other and promote each other, so that the good effect of degrading crude polysaccharide can be achieved.

According to the invention, fermentation and extraction under a low-oxygen condition are beneficial to the proliferation and growth of the facultative anaerobes, and meanwhile, the extraction under the low-oxygen condition can effectively prevent oxidation of substances, so that the generated bioactive substances can play a better role.

The biological activity of polysaccharides depends on the molecular properties of the polymer, including the molecular weight of monosaccharides, the conformation of polysaccharide chains, the degree of polymerization of branched chains, and the type of glycosidic bonds. According to that present invention, the fermented *Auricularia auricula* polysaccharide is subject to phosphorylation modification, and the structure is changed after the chemical group substitutes the hydroxyl group on the polysaccharide, so that more hydroxyl groups are exposed, the antioxidant activity is enhanced, and the anti-inflammatory, anti-aging, hypoglycemic and other effects of the polysaccharide are improved; and meanwhile, the solubility of the polysaccharide is further improved, such that the polysaccharide is more easily absorbed.

The refined *Auricularia auricula* polysaccharide after deproteinization and decolorization further reacts with zinc salt, chelating groups such as the hydroxyl group and the like on the surface coordinate with Zn ions through complexation to form a stable polysaccharide-zinc compound, and the polysaccharide-zinc compound has the effects of reducing blood fat, regulating total cholesterol and effectively improving HDL cholesterol.

The preparation method of the *Auricularia auricula* polysaccharide is simple, the extraction efficiency is high, the purity of the *Auricularia auricula* polysaccharide is high, the dissolubility is good, the absorption is easy, and the physiological activity is good; and the second phase clinical test of American FDA standard proves that the Auricular auricular polysaccharide not only has very good effects of oxidation resistance, inflammation resistance, aging resistance, blood sugar reduction and the like, but also has the effects of improving the immunity, promoting the intellectual development, as well as the effects of reducing blood fat, regulating total cholesterol and effectively improving HDL cholesterol, and has wide application prospect.

DESCRIPTIONS OF DRAWING

In order to more clearly illustrate the embodiments of the present invention or the technical solutions in the prior art, the following will briefly introduce the figures used in the description of the embodiments or the prior art. Obviously, the figures in the following description are only some embodiments of the present invention. For those of ordinary skill in the art, without creative work, other figures may also be derived from these figures.

SPECIFIC IMPLEMENTATION METHODS

Figure 1:
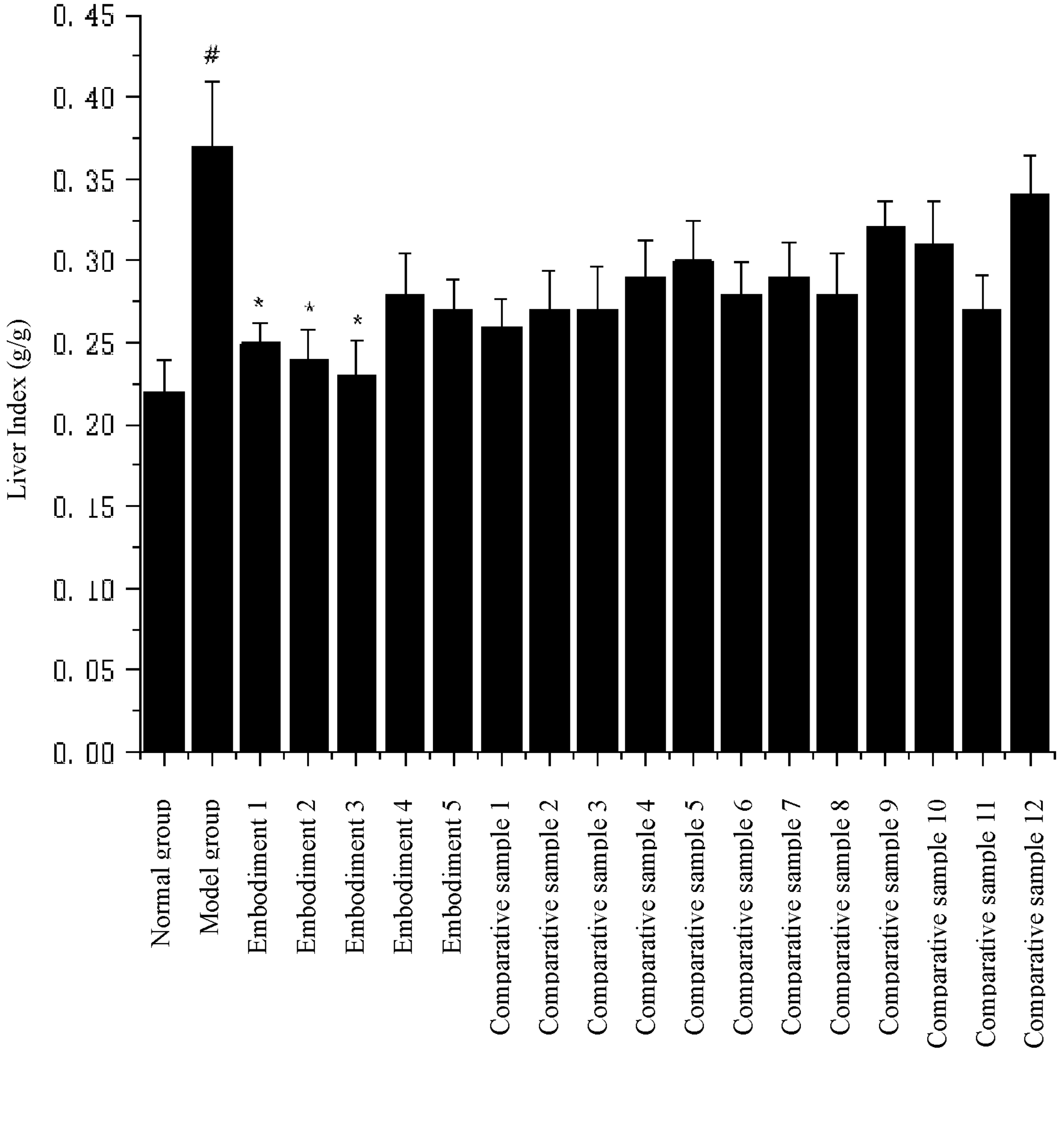
FIG. 1 is a graph showing a comparison of liver indexes of respective groups of mice in test example 4 of the present invention.

The technical solutions in the embodiments of the invention will be described clearly and completely below, and it is clear that the embodiments described are only a part of the embodiments of the invention and not all of them. Based on the embodiments of the present invention, all other embodiments obtained by those of ordinary skill in the art without the creative work belong to the scope of protection of the present invention.

Snailase with wall-breaking rate of 80%-90% and optimum pH of 5.8-7.2 is purchased from China Biotechnology Co., Ltd. The β-glucanase with 20000 U/g is purchased from Henan Wanbang Industrial Co., Ltd. The α-glucosidase with 20000 U/g is purchased from Shanghai Yuanye Bio-Technology Co., Ltd.

*Lactobacillus bulgaricus* with the strain number of *Lactobacillus bulgaricus* LB-Z16, *Streptococcus thermophilus* with the strain number of *Streptococcus thermophilus* STN26, and *Bifidobacterium longum* with the strain number of *Bifidobacterium longum* BLG-19 are all purchased from Shandong Zhongke Jiayi Bioengineering Co., Ltd.

The Sevage reagent is prepared and used immediately, and is obtained by uniformly mixing chloroform and n-butanol according to the volume ratio of 5:1.

Embodiment 1

The embodiment provides an *Auricularia auricula* polysaccharide, which is prepared by the follow steps:

S1. Degreasing: drying and crushing the *Auricularia auricula*, and then degreasing the *Auricularia auricula* by a supercritical fluid extraction process to obtain the degreased *Auricularia auricula*; wherein the conditions of the supercritical fluid extraction process are as follows: the flow rate of $CO_2$ is 7 L/h, the pressure of an extraction kettle is 12 MPa, the temperature is 45 deg C., and the extraction time is 1 h;

S2. Preliminary enzymolysis: 100 parts by weight of degreased *Auricularia auricula* in the step S1 are added into 200 parts by weight of water, 3 part by weight of snailase is added, enzymolysis is performed for 1 h at 40 deg C., the enzyme is inactivated for 10 min at 100 deg C., an organic film is concentrated to ⅓ of the original volume, and the material is dried at 70 deg C. for 2 h to obtain the preliminary enzymolysis product;

S3. extraction under ultrasound in combination with $H_2O_2$: 100 parts by weight of the preliminary enzymolysis product obtained in the step S2 is added to 100 parts by weight of 2 wt % $H_2O_2$ solution, ultrasonic treatment is performed for 30 min at 1500 W, 7 parts by weight sodium bisulfite is added to remove $H_2O_2$, alcohol precipitation is performed, centrifuging is performed at 3000 r/min for 15 min, and the material is dried at 70 deg C. for 2 h to obtain the *Auricularia auricula* raw sugar extract;

S4. secondary enzymolysis: 100 parts by weight of the raw sugar extract prepared in the step S3 is dissolved in 100 parts by weight of water, 5 parts of complex enzyme is added, enzymolysis is performed for 3 hours at 40 deg C., and the enzyme is inactivated for 10 minutes at 100 deg C. to obtain the secondary enzymolysis extract; wherein the complex enzyme is the compound mixture of β-glucanase and α-glucosidase, and the mass ratio is 3:1;

S5. Activation of strains: *Lactobacillus bulgaricus, Streptococcus thermophilus* and *Bifidobacterium longum* are respectively streaked in Gauze's medium, and activating and culturing are performed at 40 deg C. for 18 h under the low-oxygen condition to obtain the strain seed liquid with the bacteria content of $10^8$ cfu/mL;

S6. Fermentation: the strain seed liquid prepared in the step S5 is inoculated into the secondary enzymolysis extract solution prepared in the step S4, wherein the inoculum sizes of *Lactobacillus bulgaricus, Streptococcus thermophilus* and *Bifidobacterium longum* are 3%, 1% and 1% respectively, fermenting and culturing are carried out at 40 deg C. for 36 h under the low-oxygen condition, concentrating is performed, alcohol precipitation is performed, and the material is centrifuged at 3000 r/min for 15 min to obtain the fermented *Auricularia auricula* polysaccharide; wherein the low-oxygen condition is that the content of $O_2$ is 5%, the content of $CO_2$ is 5%, and the remanent is nitrogen, wherein % is the volume percentage content;

S7. Phosphorylation: 10 parts by weight of the fermented polysaccharide prepared in the step S6 is added into 100 parts by weight of water, 30 parts by weight of sodium sulfate and 2 parts by weight of the phosphorylation reagent are added, the pH value is adjusted to 8.8, the material is heated at 70 deg C. to react for 3 h, dialyzed for 24 h by using the dialysis bag with the pore size of 5000 Da, and the organic membrane is concentrated to ⅓ of the original volume to obtain phosphorylated *Auricularia auricula* polysaccharide solution; wherein the phosphorylation reagent is a mixture of sodium tripolyphosphate, sodium trimetaphosphate and pyrophosphoric acid in a mass ratio of 3:2:0.2; alcohol precipitation is further performed on the phosphorylated *Auricularia auricula* polysaccharide solution and centrifuging is performed at 3000 r/min for 15 min, infrared spectral scanning is performed on a solid freeze-dried sample showed that the absorption peak of —OH is at 3340 $cm^{-1}$, the asymmetric stretching vibration peak of $CH_2$ is at 2911 $cm^{-1}$, and the C═O vibration peak is at 1612 $cm^{-1}$, the stretching vibration peak of P═O is at 1201 $cm^{-1}$, and the characteristic absorption peak of P—O—C is at 887 $cm^{-1}$, which can be seen that a phosphate group is successfully connected to a polysaccharide molecular chain.

S8. Deproteinization: 10 parts by weight of the phosphorylated *Auricularia auricula* polysaccharide solution obtained in the step S7 is added into the 30 parts by weight of Sevage reagent, stirred for the reaction for 20 min, centrifuged to remove denatured protein precipitate, the steps are repeated for 1 time, the liquids are merged, and the solvent is removed under reduced pressure to obtain the deproteinized *Auricularia auricula* polysaccharide;

S9. Decolorization: 12 parts by weight of activated carbon and 100 parts by weight of deproteinized *Auricularia auricula* polysaccharide prepared in the step S8 are added into 200 parts by weight of water, stirred and adsorbed for 30 min, and filtered, alcohol precipitation is performed, and centrifuging is performed at 3000 r/min for 15 min to obtain the refined *Auricularia auricula* polysaccharide;

S10. Zinc chelating: 100 parts by weight of the refined *Auricularia auricula* polysaccharide prepared in step S9 and 5 parts by weight of trisodium citrate are dissolved in 200 parts by weight of water, 22 parts by weight of zinc salt is added, the pH value of the solution is adjusted to 7.2, the materials are heated to 45 deg C. and stirred for the reaction at 300 r/min for 1 h, and filtered, alcohol precipitation is performed, the material is centrifuged at 3000 r/min for 15 min, solid is collected, and freeze-drying is performed to obtain the *Auricularia auricula* polysaccharide; wherein an alcohol precipitation method in this embodiment is to add absolute ethanol until the ethanol content in the system is 75%, and precipitate for 12 h.

Embodiment 2

The embodiment provides an *Auricularia auricula* polysaccharide, which is prepared by the follow steps:

S1. Degreasing: drying and crushing the *Auricularia auricula*, and then degreasing the *Auricularia auricula* by a supercritical fluid extraction process to obtain the degreased *Auricularia auricula*; wherein the conditions of the supercritical fluid extraction process are as follows: the flow rate of $CO_2$ is 12 L/h, the pressure of an extraction kettle is 25 MPa, the temperature is 60 deg C., and the extraction time is 2 h;

S2. Preliminary enzymolysis: 100 parts by weight of degreased *Auricularia auricula* in the step S1 are added into 200 parts by weight of water, 5 parts by weight of snailase is added, enzymolysis is performed for 2 h at 50 deg C., the enzyme is inactivated for 15 min at 110 deg C., an organic film is concentrated to ¼ of the original volume, and the material is dried at 70 deg C. for 2 h to obtain the preliminary enzymolysis product;

S3. Extraction under ultrasound in combination with $H_2O_2$: 100 parts by weight of the preliminary enzymolysis product obtained in the step S2 is added to 100 parts by weight of 5 wt % $H_2O_2$ solution, ultrasonic treatment is performed for 50 min at 2000 W, 12 parts by weight sodium bisulfite is added to remove $H_2O_2$, alcohol precipitation is performed, the materials are centrifuged at 3000 r/min for 15 min, and dried at 70 deg C. for 2 h to obtain the *Auricularia auricula* raw sugar extract;

S4. Secondary enzymolysis: 100 parts by weight of the raw sugar extract prepared in the step S3 is dissolved in 100 parts by weight of water, 7 parts of complex enzyme is added, enzymolysis is performed for 5 h at 45 deg C., and the enzyme is inactivated for 15 min at 110 deg C. to obtain the secondary enzymolysis extract; wherein the complex enzyme is the compound mixture of β-glucanase and α-glucosidase, and the mass ratio is 5:1;

S5. Activation of strains: *Lactobacillus bulgaricus, Streptococcus thermophilus* and *Bifidobacterium longum* are respectively streaked in Gauze's medium, and activating and culturing are performed at 45 deg C. for 24 h under the low-oxygen condition to obtain the strain seed liquid with the bacteria content of $10^9$ cfu/mL;

S6. Fermentation: the strain seed liquid prepared in the step S5 is inoculated into the secondary enzymolysis extract solution prepared in the step S4, wherein the inoculum sizes of *Lactobacillus bulgaricus, Streptococcus thermophilus* and *Bifidobacterium longum* are 5%, 3% and 2% respectively, fermenting and culturing are carried out at 45 deg C. for 48 h under the low-oxygen condition, concentrating is performed, alcohol precipitation is performed, and the material is centrifuged at 3000 r/min for 15 min to obtain the fermented *Auricularia auricula* polysaccharide;

the low-oxygen condition is that the content of $O_2$ is 7%, the content of $CO_2$ is 10%, and the remanent is nitrogen, wherein % is the volume percentage content;

S7. Phosphorylation: 10 parts by weight of the fermented polysaccharide prepared in the step S6 is added into 100 parts by weight of water, 50 parts by weight of sodium sulfate and 4 parts by weight of the phosphorylation reagent are added, the pH value is adjusted to 9.2, the material is heated at 90 deg C. to react for 5 h, dialyzed for 48 h by using the dialysis bag with the pore size of 15000 Da, and the organic membrane is concentrated to ¼ of the original volume to obtain the phosphorylated *Auricularia auricula* polysaccharide solution; wherein the phosphorylation reagent is a mixture of sodium tripolyphosphate, sodium trimetaphosphate and pyrophosphoric acid in a mass ratio of 7:2:0.4;

S8. Deproteinization: 10 parts by weight of the phosphorylated *Auricularia auricula* polysaccharide solution obtained in the step S7 is added into the 70 parts by weight of Sevage reagent, stirred for the reaction for 30 min, centrifuged to remove denatured protein precipitate, the steps are repeated for 3 time, the liquids are merged, and the solvent is removed under reduced pressure to obtain the deproteinized *Auricularia auricula* polysaccharide;

S9. Decolorization: 15 parts by weight of activated carbon and 100 parts by weight of deproteinized *Auricularia auricula* polysaccharide prepared in the step S8 are added into 200 parts by weight of water, stirred and adsorbed for 50 min, and filtered, alcohol precipitation is performed, and centrifuging is performed at 3000 r/min for 15 min to obtain refined *Auricularia auricula* polysaccharide;

S10. Zinc chelating: 100 parts by weight of the refined *Auricularia auricula* polysaccharide prepared in step S9 and 12 parts by weight of trisodium citrate are dissolved in 200 parts by weight of water, 27 parts by weight of zinc salt is added, the pH value of the solution is adjusted to 7.5, the material is heated to 55 deg C. and stirred for the reaction at 500 r/min for 2 h, and filtered, alcohol precipitation is performed, the material is centrifuged at 3000 r/min for 15 min, solid is collected, and freeze-drying is performed to obtain the *Auricularia auricula* polysaccharide; wherein an alcohol precipitation method in this embodiment is to add absolute ethanol until the ethanol content in the system is 85%, and precipitate for 24 h.

Embodiment 3

The embodiment provides an *Auricularia auricula* polysaccharide, which is prepared by the follow steps:

S1. Degreasing: drying and crushing the *Auricularia auricula*, and then degreasing the *Auricularia auricula* by a supercritical fluid extraction process to obtain the degreased *Auricularia auricula*; wherein the conditions of the supercritical fluid extraction process are as follows: the flow rate of $CO_2$ is 10 L/h, the pressure of an extraction kettle is 17 MPa, the temperature is 52 deg C., and the extraction time is 1.5 h;

S2. Preliminary enzymolysis: 100 parts by weight of degreased *Auricularia auricula* in the step S1 are added into 200 parts by weight of water, 4 part by weight of snailase is added, enzymolysis is performed for 1.5 h at 45 deg C., the enzyme is inactivated for 12 min at 105 deg C., the organic film is concentrated to ¼ of the original volume, and the material is dried at 70 deg C. for 2 h to obtain the preliminary enzymolysis product;

S3. Extraction under ultrasound in combination with $H_2O_2$: 100 parts by weight of the preliminary enzymolysis product obtained in the step S2 is added to 100 parts by weight of 3.5 wt % $H_2O_2$ solution, ultrasonic treatment is performed for 40 min at 1700 W, 10 parts by weight sodium bisulfite is added to remove $H_2O_2$, alcohol precipitation is performed, centrifuging is performed at 3000 r/min for 15 min, and the material is dried at 70 deg C. for 2 h to obtain the *Auricularia auricula* raw sugar extract;

S4. Secondary enzymolysis: 100 parts by weight of the raw sugar extract prepared in the step S3 is dissolved in 100 parts by weight of water, 6 parts of complex enzyme is added, enzymolysis is performed for 4 hours at 42 deg C., and the enzyme is inactivated for 12 minutes at 105 deg C. to obtain the secondary enzymolysis extract; wherein the complex enzyme is the compound mixture of β-glucanase and α-glucosidase, and the mass ratio is 4:1;

S5. Activation of strains: *Lactobacillus bulgaricus, Streptococcus thermophilus* and *Bifidobacterium longum* are respectively streaked in Gauze's medium, and activating and culturing are performed at 42 deg C. for 21 h under the low-oxygen condition to obtain the strain seed liquid with the bacteria content of $10^9$ cfu/mL;

S6. Fermentation: the strain seed liquid prepared in the step S5 is inoculated into the secondary enzymolysis extract solution prepared in the step S4, wherein the inoculum sizes of *Lactobacillus bulgaricus, Streptococcus thermophilus* and *Bifidobacterium longum* are 4%, 2% and 1.5% respectively, fermenting and culturing are carried out at 42 deg C. for 42 h under the low-oxygen condition, concentrating is performed, alcohol precipitation is performed, and the material is centrifuged at 3000 r/min for 15 min to obtain the fermented *Auricularia auricula* polysaccharide; the low-oxygen condition is that the content of 02 is 6%, the content of $CO_2$ is 7%, and the remanent is nitrogen, wherein % is the volume percentage content;

S7. Phosphorylation: 10 parts by weight of the fermented polysaccharide prepared in the step S6 is added into 100 parts by weight of water, 40 parts by weight of sodium sulfate and 3 parts by weight of the phosphorylation reagent are added, the pH value is adjusted to 9, the material is heated at 80 deg C. to react for 4 h, dialyzed for 36 h by using the dialysis bag with the pore size of 10000 Da, and the organic membrane is concentrated to ¼ of the original volume to obtain phosphorylated *Auricularia auricula* polysaccharide solution; wherein the phosphorylation reagent is a mixture of sodium tripolyphosphate, sodium trimetaphosphate and pyrophosphoric acid in a mass ratio of 5:2:0.3;

S8. Deproteinization: 10 parts by weight of the phosphorylated *Auricularia auricula* polysaccharide solution obtained in the step S7 is added into the 50 parts by weight of Sevage reagent, stirred for the reaction for 25 min, centrifuged to remove denatured protein precipitate, the steps are repeated for 2 times, the liquids are merged, and the solvent is removed under reduced pressure to obtain the deproteinized *Auricularia auricula* polysaccharide;

S9. Decolorization: 13 parts by weight of activated carbon and 100 parts by weight of deproteinized *Auricularia auricula* polysaccharide prepared in the step S8 are added into 200 parts by weight of water, stirred and adsorbed for 40 min, and filtered, alcohol precipitation is performed, and centrifuging is performed at 3000 r/min for 15 min to obtain refined *Auricularia auricula* polysaccharide;

S10. Zinc chelating: 100 parts by weight of the refined *Auricularia auricula* polysaccharide prepared in step S9 and 9 parts by weight of trisodium citrate are dissolved in 200 parts by weight of water, 25 parts by weight of zinc salt is added, the pH value of the solution is adjusted to 7.3, the material is heated to 50 deg C. and stirred for the reaction at 400 r/min for 1.5 h, and filtered, alcohol precipitation is performed, the material is centrifuged at 3000 r/min for 15 min, solid is collected, and freeze-drying is performed to obtain the *Auricularia auricula* polysaccharide; wherein an alcohol precipitation method in this embodiment is to add absolute ethanol until the ethanol content in the system is 80%, and precipitate for 18 h.

Embodiment 4

Compared with the embodiment 3, the complex enzyme is a single β-glucanase, and the other conditions are not changed.

Embodiment 5

Compared with the embodiment 3, the complex enzyme is a single α-glucanase, and the other conditions are not changed.

Comparative Example 1

Compared with the embodiment 3, the preliminary enzymolysis in step S2 is not performed, and the other conditions are not changed.

Comparative Example 2

Compared with the embodiment 3, the 3.5 wt % $H_2O_2$ solution in step S3 is substituted with the same amount of water, and other conditions are not changed.

Comparative Example 3

Compared with the embodiment 3, the ultrasonic treatment is not performed in step S3, and the other conditions are not changed.

Comparative Example 4

Compare with the embodiment 3, the extraction under ultrasound in combination with $H_2O_2$ is not performed in the step S3, and the extraction condition are not changed.

Comparative Example 5

Compared with the embodiment 3, the secondary enzymolysis in step S4 is not performed, and the other conditions are not changed.

Comparative Example 6

Compared with the embodiment 3, *Lactobacillus bulgaricus* is not inoculated in step S6, and the other conditions are not changed.

The inoculum sizes of *Streptococcus thermophilus* and *Bifidobacterium longum* are 6% and 1.5% respectively.

Comparative Example 7

Compared with the embodiment 3, *Streptococcus thermophilus* is not inoculated in step S6, and the other conditions are not changed.

The inoculum sizes of *Lactobacillus bulgaricus* and *Bifidobacterium longum* are 6% and 1.5% respectively.

Comparative Example 8

Compared with the embodiment 3, *Bifidobacterium longum* is not inoculated in step S6, and the other conditions are not changed.

The inoculum sizes of *Lactobacillus bulgaricus, Streptococcus thermophilus* and *Bifidobacterium longum* are 4% and 3.5% respectively.

Comparative Example 9

Compared with the embodiment 3, the steps S5 and S6 are not performed, and the other conditions are not changed.

Comparative Example 10

Compared with the embodiment 3, the step S7 phosphorylation is not performed, and the other conditions are not changed.

Comparative Example 11

Compared with the embodiment 3, the step S8 deproteinization is not performed, and the other conditions are not changed.

Comparative Example 12

Compared with the embodiment 3, the step S10 zinc chelating is not performed, and the other conditions are not changed.

Test Example 1: Determination of Polysaccharide Extraction Yield

By adopting a phenol-sulfuric acid method for testing, about 100 mg of the refined *Auricularia auricula* polysaccharide sample prepared in the steps S9 of the embodiments 1-5 and the comparative examples 1-11 are respectively taken and put in a test tube, water is added to supplement the sample to 2.0 mL, then 1.0 mL of 6% phenol is respectively added, the sample is shaken evenly, 5.0 mL of 98 wt % concentrated sulfuric acid is dripped in 10 s, the sample is quickly shaken evenly, the sample is kept stand for 15 min and shaken evenly, the sample is kept stand for 30 min at room temperature, the absorbance of the sample at 490 nm is measured, and 2.0 mL of water is used as a blank control according to the same operation. According to the OD value of the sample, the standard curve is drawn by the same method with different concentrations of glucose, and the regression equation is y=12. 974x+0.0125, $R^2$=0.9991. According to the standard curve, the polysaccharide content C in each group of polysaccharide samples is obtained, and the yield (%) of each group of the *Auricularia auricula* polysaccharide is calculated.

The yield of *Auricularia auricula* polysaccharide (%)=$CVM_1/M_2M_0$×100%

In the formula, C represents the polysaccharide content (mg/mL) in the polysaccharide sample; $M_1$ represents the weight (g) of the polysaccharide sample; $M_0$ represents the weight (g) of *Auricularia auricula* in step S1; V represents the total volume (mL) of the solution, i.e., 2 mL; and $M_2$ represents the weight (mg) of the refined *Auricularia auricula* polysaccharide sample.

The results are shown in Table 1.

| Group | Extraction rate (%) |
|---|---|
| Embodiment 1 | 7.56 |
| Embodiment 2 | 7.62 |
| Embodiment 3 | 7.70 |
| Embodiment 4 | 7.22 |
| Embodiment 5 | 7.18 |
| Comparative example 1 | 7.31 |
| Comparative example 2 | 7.04 |
| Comparative example 3 | 6.98 |
| Comparative example 4 | 6.52 |
| Comparative example 5 | 7.07 |
| Comparative example 6 | 7.34 |
| Comparative example 7 | 7.28 |
| Comparative example 8 | 7.32 |
| Comparative example 9 | 7.25 |
| Comparative example 10 | 7.39 |
| Comparative example 11 | 7.19 |

It can be seen from the above table that the extraction rate of polysaccharides in the embodiments 1-3 of the present invention is higher, which is significantly better than that in the embodiments 4-5 and the comparative examples 1-11.

Test Example 2: Determination of Solubility

The solubility of the *Auricularia auricula* polysaccharide prepared in the embodiments 1-5 and the comparative examples 1-12 and the commercially available *Auricularia auricula* polysaccharide (with a content of more than 99%, purchased from Lanzhou Wote Laisi Biotechnology Co., Ltd.) is measured according to the method of Pharmacopoeia 2005, and the results are shown in Table 2.

TABLE 2

| Group | Solubility (mg/100 g) |
|---|---|
| Commercially available | 0.12 |
| Embodiment 1 | 267 |
| Embodiment 2 | 262 |
| Embodiment 3 | 275 |
| Embodiment 4 | 232 |
| Embodiment 5 | 226 |
| Comparative example 1 | 238 |
| Comparative example 2 | 241 |
| Comparative example 3 | 236 |
| Comparative example 4 | 231 |
| Comparative example 5 | 205 |
| Comparative example 6 | 232 |
| Comparative example 7 | 227 |
| Comparative example 8 | 233 |
| Comparative example 9 | 221 |
| Comparative example 10 | 197 |
| Comparative example 11 | 234 |
| Comparative example 12 | 217 |

It can be seen from the above table that the solubility of the *Auricularia auricula* polysaccharide prepared by the method described in the embodiments 1-3 of the present invention is significantly improved.

Test Example 3

The *Auricularia auricula* polysaccharides prepared in the embodiments 1 to 5 and the comparative examples 1 to 12 are subjected to an antioxidant test.

1. DPPH Free Radical Scavenging Capacity 3 mL of 10 mmol/L DPPH-ethanol solution, 1 mL of 1 mg/mL polysaccharide sample solution prepared with water from *Auricularia auricula* polysaccharide prepared in the embodiments 1-5 or the comparative examples 1-12 or 1 mg/mL vitamin C solution are added into a colorimetric tube in turn, the colorimetric tube is shaken uniformly, and then kept stand in the dark for 30 min. The absorbance is determined at 517 nm and record as $A_1$;

3 mL of 5 mmol/L DPPH-ethanol solution and 1 mL of absolute ethanol are added into the colorimetric tube, the colorimetric tube is shaken uniformly, and then kept stand in the dark for 30 min. The absorbance is determined at 517 nm and record as $A_0$;

3 mL of distilled water and 1 mL of 1 mg/mL polysaccharide sample solution prepared with water from *Auricularia auricula* polysaccharide prepared in the embodiments 1-5 or the comparative examples 1-12 are added into a colorimetric tube in turn, the colorimetric tube is shaken uniformly, and then kept stand in the dark for 30 min. The absorbance is determined at 517 nm and record as $A_2$;

$$DPPH \text{ free radical scavenging rate}(\%) = \left[1 - (A_1 - A_2)/A_0\right] \times 100\%$$

2. Hydroxyl Free Radical Scavenging Capacity 1 mL of 10 mmol/L $FeSO_4$, 1 mL of 20 mmol/L a-desoxyribose solution, 1 mL of 1 mg/mL polysaccharide sample solution prepared with water from *Auricularia auricula* polysaccharide prepared in the embodiments 1-5 or the comparative examples 1-12 or 1 mg/mL of vitamin C solution are added into the colorimetric tube in turn, 1 mL of 10 mmol/L $H_2O_2$ is added, the colorimetric tube is shaken uniformly, the materials are reacted at 37 deg C. for 30 min, and the absorbance of the sample solution is determined at 510 nm, which is recorded as $A_1$.

1 mL of 9 mmol/L $FeSO_4$, 1 mL of 9 mmol/L salicylic acid-ethanol solution and 1 mL distilled water are added into the colorimetric tube, 1 mL of 8.8 mmol/L $H_2O_2$ is added, the colorimetric tube is shaken uniformly, the materials are reacted for 30 min at 37 deg C., and the absorbance of the sample solution is determined at 510 nm, which is recorded as $A_0$;

1 mL of 9 mmol/L $FeSO_4$, 1 mL of 9 mmol/L salicylic acid-ethanol solution, 1 mL of 1 mg/mL polysaccharide sample solution prepared with water from *Auricularia auricula* polysaccharide prepared in the embodiments 1-5 or the comparative examples 1-12 or 1 mg/mL of vitamin C solution are added into the colorimetric tube in turn, 1 mL of distilled water is added, the colorimetric tube is shaken uniformly, the materials are reacted at 37 deg C. for 30 min, and the absorbance of the sample solution is determined at 510 nm, which is recorded as $A_2$.

$$\text{Hydroxyl free radical scavenging rate(\%)} = [1 - (A_1 - A_2)/A_0] \times 100\%$$

3. Superoxide Anion Free Radical Scavenging Ability 3 mL of 0.05 mol/L Tris-HCl buffer solution with the pH value of 7.4, 1 mL of 1 mL of the polysaccharide sample solution prepared with water from *Auricularia auricula* polysaccharide prepared in the embodiments 1-5 or the comparative examples 1-12, or 1 mg/mL of vitamin C solution, and 2 mL of 60 mmol/L pyrogallol solution are added into the colorimetric tube in turn, the materials are mixed in 10 s, and the absorbance is determined at 325 nm every 30 s until 300 s, $A_0=A_{300s}-A_{30s}$; the sample solution is substituted with 1 mL of distilled water, and the absorbance at 325 nm is determined, $A_1=A_{300s}-A_{30s}$.

$$\text{Superoxide anion free radical scavenging rate (\%)}=(A_0-A_1)/A_1\times100\%$$

The results are shown in Table 3.

TABLE 3

| Group | DPPH free radical scavenging rate (%) | Hydroxyl free radical scavenging rate (%) | Superoxide anion free radical scavenging rate (%) |
|---|---|---|---|
| Embodiment 1 | 93.7 | 90.1 | 88.9 |
| Embodiment 2 | 94.1 | 91.5 | 89.8 |
| Embodiment 3 | 94.7 | 92.2 | 90.4 |
| Embodiment 4 | 88.7 | 85.6 | 84.1 |
| Embodiment 5 | 87.9 | 84.5 | 83.7 |
| Comparative example 1 | 90.2 | 86.0 | 84.7 |
| Comparative example 2 | 86.5 | 83.2 | 82.5 |
| Comparative example 3 | 85.1 | 82.2 | 81.4 |
| Comparative example 4 | 82.4 | 78.9 | 77.6 |
| Comparative example 5 | 84.2 | 81.1 | 80.4 |
| Comparative example 6 | 89.7 | 85.3 | 83.5 |
| Comparative example 7 | 88.4 | 84.1 | 82.1 |
| Comparative example 8 | 89.3 | 85.0 | 83.1 |
| Comparative example 9 | 86.5 | 82.2 | 81.7 |
| Comparative example 10 | 83.4 | 80.6 | 79.3 |
| Comparative example 11 | 92.0 | 89.2 | 87.9 |
| Comparative example 12 | 82.7 | 78.9 | 77.4 |
| Vitamin C | 66.5 | 60.2 | 57.9 |

It can be seen from the above table that the *Auricularia auricula* polysaccharides prepared in the embodiments 1-3 of the present invention have good antioxidant activity and high scavenging rates on DPPH free radicals, hydroxyl free radicals and superoxide anion free radicals.

Test Example 3: Hypolipidemic Test

Healthy male SD rats aged 7 weeks are selected for adaptive feeding at 22±3 deg C. and 60±10% relative humidity for one week. One week later, the rats are randomly and averagely divided into 19 groups, namely a normal group, a model group, embodiment groups 1-5, and comparative example groups 1-12, with 6 rats in each group for 6 weeks of intervention feeding. The normal group is fed with conventional feed, and the other groups are fed with high-fat feed. The rats in the embodiment groups 1-5 and the comparative example groups 1-12 are fed with 200 mg/kg of *Auricularia auricula* polysaccharide once a day by a gavage method, 2 mL is required for each time, and the rats in the model group are fed with the same amount of normal saline by the gavage method. During the experiment, the rats are free to eat and drink, and weighed every 5 d.

The rats in each group are weighed at the beginning of intervention (0 week). At the end of the experiment (6 weeks), the rats are fasted overnight for 12 hours, and 1 mL of blood is taken from the tip of the tail the next day. After centrifugation, a supernatant is taken as a serum sample. The rats in each group are then randomly dissected, and liver tissues are isolated and weighed. The concentrations of total cholesterol (TC), triglyceride (TG), high density lipoprotein cholesterol (HDL-C) and low density lipoprotein cholesterol (LDL-C) in rat plasma are detected by a kit method, and the ratio of HDL-C/TC is calculated.

The results are shown in Table 4.

| Group | TC (mmol/L) | TG (mmol/L) | HDL-C (mmol/L) | LDL-C (mmol/L) | HDL-C/TC |
|---|---|---|---|---|---|
| Normal group | 1.52 ± 0.15 | 0.32 ± 0.11 | 1.51 ± 0.21 | 0.37 ± 0.09 | 0.99 |
| Model group | 4.11 ± 0.62# | 0.58 ± 0.21# | 1.12 ± 0.14# | 1.08 ± 0.32# | 0.27 |
| Embodiment 1 | 1.81 ± 0.17* | 0.41 ± 0.13* | 1.42 ± 0.20* | 0.41 ± 0.11* | 0.78 |
| Embodiment 2 | 1.78 ± 0.13* | 0.39 ± 0.10* | 1.44 ± 0.24* | 0.43 ± 0.10* | 0.80 |

-continued

| Group | TC (mmol/L) | TG (mmol/L) | HDL-C (mmol/L) | LDL-C (mmol/L) | HDL-C/TC |
|---|---|---|---|---|---|
| Embodiment 3 | 1.75 ± 0.19* | 0.38 ± 0.08* | 1.45 ± 0.21* | 0.44 ± 0.06* | 0.82 |
| Embodiment 4 | 1.95 ± 0.16 | 0.43 ± 0.12 | 1.37 ± 0.20 | 0.48 ± 0.09 | 0.70 |
| Embodiment 5 | 1.97 ± 0.12 | 0.44 ± 0.09 | 1.38 ± 0.18 | 0.49 ± 0.11 | 0.70 |
| Comparative example 1 | 1.92 ± 0.16 | 0.43 ± 0.15 | 1.39 ± 0.15 | 0.47 ± 0.14 | 0.72 |
| Comparative example 2 | 1.99 ± 0.11 | 0.44 ± 0.13 | 1.37 ± 0.23 | 0.50 ± 0.12 | 0.69 |
| Comparative example 3 | 2.02 ± 0.18 | 0.45 ± 0.11 | 1.36 ± 0.22 | 0.52 ± 0.08 | 0.67 |
| Comparative example 4 | 2.10 ± 0.20 | 0.47 ± 0.12 | 1.31 ± 0.21 | 0.56 ± 0.07 | 0.62 |
| Comparative example 5 | 2.02 ± 0.24 | 0.46 ± 0.08 | 1.33 ± 0.16 | 0.54 ± 0.09 | 0.66 |
| Comparative example 6 | 1.95 ± 0.12 | 0.44 ± 0.14 | 1.37 ± 0.14 | 0.48 ± 0.12 | 0.70 |
| Comparative example 7 | 1.99 ± 0.14 | 0.45 ± 0.11 | 1.32 ± 0.19 | 0.50 ± 0.11 | 0.66 |
| Comparative example 8 | 1.96 ± 0.21 | 0.44 ± 0.13 | 1.36 ± 0.15 | 0.49 ± 0.14 | 0.69 |
| Comparative example 9 | 2.07 ± 0.24 | 0.47 ± 0.08 | 1.29 ± 0.16 | 0.55 ± 0.12 | 0.62 |
| Comparative example 10 | 1.94 ± 0.15 | 0.44 ± 0.06 | 1.35 ± 0.19 | 0.48 ± 0.09 | 0.70 |
| Comparative example 11 | 1.92 ± 0.18 | 0.43 ± 0.09 | 1.32 ± 0.13 | 0.46 ± 0.10 | 0.69 |
| Comparative example 12 | 2.12 ± 0.23 | 0.50 ± 0.10 | 1.29 ± 0.16 | 0.60 ± 0.15 | 0.61 |

Note:
#is compared with the normal group, P < 0.05;
*is compared with the model group, P < 0.05.

TG and TC are one of the important indexes to evaluate cholesterol metabolism, and one of the functions of HDL-C is to transport cholesterol from extrahepatic tissues back to the liver. It can be seen from the above table that the *Auricularia auricula* polysaccharide prepared in the embodiments 1-3 of the present invention can significantly reduce the contents of TC, TG and LDL-C in mouse serum and increase the content of HDL-C. At the same time, it can significantly improve the ratio of HDL-C/TC, so as to play a stable role in reducing blood fat, regulating total cholesterol and effectively improving HDL cholesterol.

The rats are dissected, their livers are separated and weighed, and the liver index is calculated.

$$\text{Liver index} = \text{liver fresh weight } (G)/\text{body weight } (G)$$

Liver index results are shown in FIG. 1. The liver is an important place for lipid metabolism, excessive fat intake will accumulate in the liver and cause liver lipid metabolism disorders, resulting in increased liver burden and increased liver weight, and the increased liver index indicates that high-fat diet causes liver damage in rats. It can be seen from the figure that the *Auricularia auricula* polysaccharide prepared in the embodiments 1-3 of the present invention can significantly reduce the liver index of the rats, which is equivalent to the level of rats in the normal group.

Figure 2:
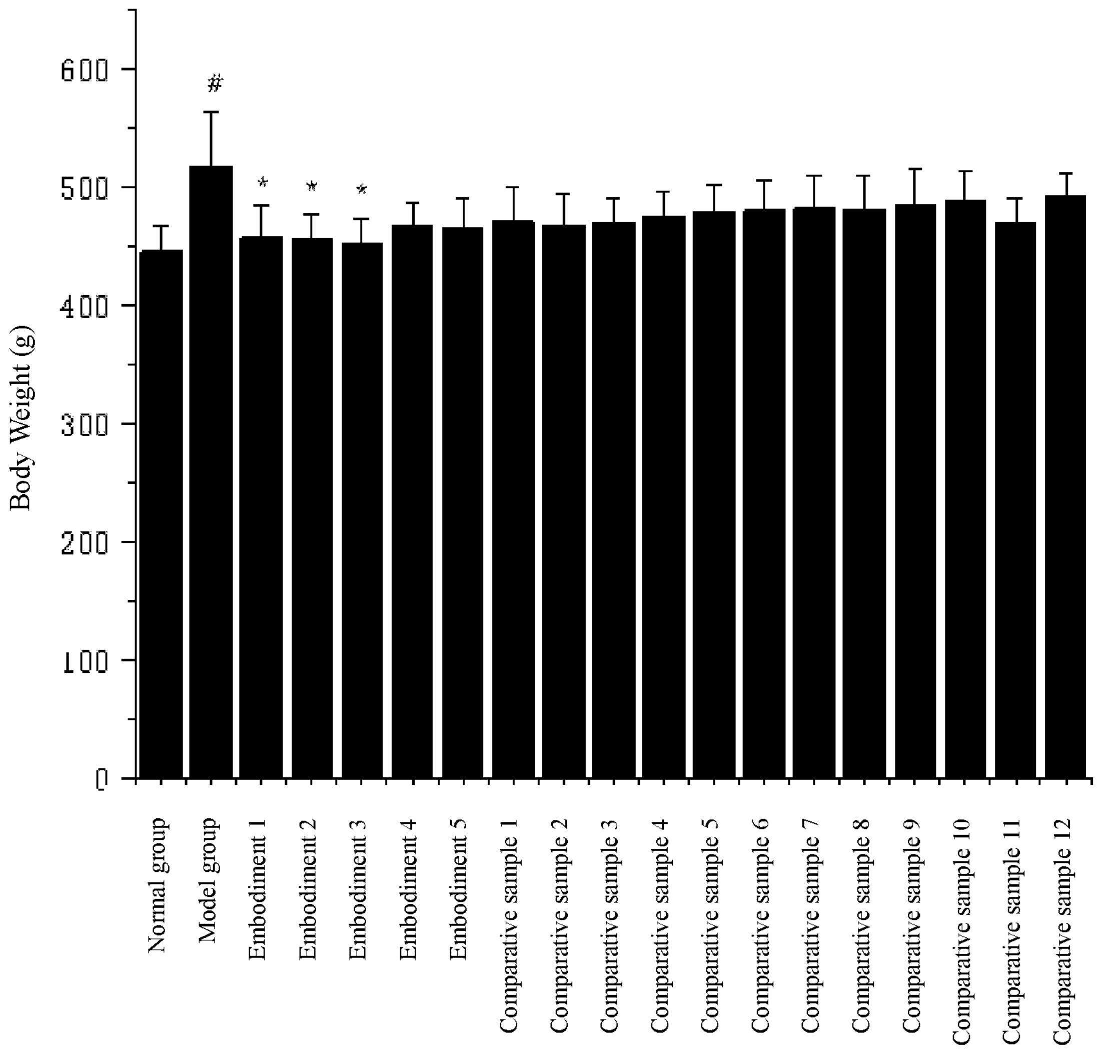
FIG. 2 is a graph showing a comparison of liver indexes of respective groups of mice in test example 4 of the present invention.

Body weight results are shown in FIG. 2. It can be seen from the figure that the *Auricularia auricula* polysaccharide prepared in the embodiments 1-3 of the present invention can significantly inhibit the increase in body weight of the rats fed with high-fat diet and prevent obesity of rats.

The embodiments 4 and 5 are compared with the embodiment 3, the complex enzyme is a single β-glucanase or α-glucosidase, the solubility of the prepared *Auricularia auricula* polysaccharide is reduced, the extraction rate is reduced, the antioxidant effect is reduced, and the contents of TC, TG and LDL-C are increased. The comparative example 5 is compared with the embodiment 3, the solubility of the *Auricularia auricula* polysaccharide prepared without the secondary enzymolysis in step S4 is significantly reduced, the extraction rate is reduced, the antioxidant effect is significantly reduced, and the contents of TC, TG, and LDL-C are significantly increased. The enzymolysis of polysaccharide is mainly realized by changing the molecular weight, molecular structure, solubility and substituents of polysaccharides, and the enzymolysis is mainly realized by changing the type, quantity and physical and chemical properties of polysaccharides, and enhancing the biological activity. The *Auricularia auricula* polysaccharide is mainly composed of water-soluble β-D-glucan, water-insoluble β-D-glucan and two kinds of acidic heteropolysaccharides, and both of water-soluble β-D-glucan and water-insoluble β-D-glucan are connected by β-1,3-glycosidic bond. The β-glucanase can degrade the β-1,3-glycosidic bond and β-1,4-glycosidic bond efficiently, and make polysaccharide modified and solubilized. α-glucosidase has the dual functions of hydrolysis and transglycosidation, hydrolysis can make the non-reducing end of α-glucoside, oligosaccharide and glucan cut the α-1,4 glycosidic bond and release glucose; transglycosidation can transfer free glucose residues to another glucose or maltose substrate by α-1,6 glycosidic bond, thus obtaining non-fermentable isomaltooligosaccharide, the digestibility of polysaccharide products can be improved and the sweetness is reduced; under the synergistic effect of the β-glucanase and the α-glucosidase, the molecular weight of the *Auricularia* auricular polysaccharide can be reduced from high molecular weight to low molecular weight, the biological activity of the *Auricularia* auricular polysaccharide can be improved, and the low molecular weight polysaccharide is more easily absorbed by a human body.

The comparative example 1 is compared with the embodiment 3, the step S2 preliminary enzymolysis is not performed, the solubility of the *Auricularia auricula* polysaccharide prepared is significantly reduced, the extraction rate is reduced, the antioxidant effect is reduced, and the contents of TC, TG, and LDL-C are increased, and the content of HDL-C is reduced. In the invention, the degreased *Auricularia auricula* after the degreasing treatment is subjected to enzymolysis by the snailase, contains a plurality of mixed enzymes with biological activities, such as a large amount of cellulase, hemicellulase, pectinase, alpha amylase, seminase, sucrase, galactanase, proteolytic enzyme, amino acid transferase and the like, and under the enzymolysis action of the snailase, it is helpful to break the cell wall of *Auricularia auricula* and release the active substance polysaccharide in its cells better.

Comparative Example 2

Compared with the embodiment 3, the 3.5 wt % $H_2O_2$ solution in step S3 is substituted with the same amount of water. Comparative example 3

Compared with the embodiment 3, ultrasonic treatment is not performed in the step 3, the solubility of the prepared *Auricularia auricula* polysaccharide is reduced, the extraction rate is reduced, and the antioxidant effect is reduced. Comparative example 4 is compared with the embodiment 3, the solubility of the *Auricularia auricula* polysaccharide prepared without the extraction under ultrasound in combination with $H_2O_2$ in step S3 is significantly reduced, the extraction rate is reduced, the antioxidant effect is significantly reduced, the contents of TC, TG, and LDL-C are significantly increased, the content of HDL-C is reduced, the body weight is increased, and the liver index is increased. The preliminary enzymolysis product after snailase enzymolysis is subjected to extraction under ultrasound in combination with $H_2O_2$, a large amount of cell walls of the preliminary enzymolysis product are broken at this time, intracellular polysaccharide is dissolved out, $H_2O_2$ is the strong oxidant and can be used as the oxidant to perform the oxidative degradation reaction on the organic compounds, but the oxidative degradation efficiency of $H_2O_2$ alone is low, and after ultrasound-assisted treatment, high quantum yield of the hydroxyl group can be generated. Ultrasonic wave can reduce the activation energy of the reaction, thus significantly increase the degradation rate and shorten the reaction time. The ultrasonic wave can promote the dissociation of $H_2O_2$, and $H_2O_2$ as a synergistic measure can effectively improve the degradation rate. The ultrasonic wave generates high-frequency physical vibration, reduces the cavitation effect caused by the internal pressure of an extraction system, and rapidly further damages the cell walls of a extract, so that more than 90% of cell walls are broken, the particle diffusion strength of active substances of the extract is increased, the friction and collision among particles are promoted to rapidly generate heat, the cell walls are damaged, the extraction time is obviously shortened, and the extraction efficiency is improved.

The comparative examples 6, 7 and 8 are compared with the embodiment 3, *Lactobacillus bulgaricus, Streptococcus thermophilus* or *Bifidobacterium longum* are not inoculated in step S6, the solubility of the prepared *Auricularia auricula* polysaccharide is reduced, the antioxidant effect is reduced, the contents of TC, TG and LDL-C are increased, the content of HDL-C is reduced, the body weight is increased, and the liver index is increased. The comparative example 9 is compared with the embodiment 3, the steps S5 and S6 are not performed, the solubility of the *Auricularia auricula* polysaccharide prepared is significantly reduced, the antioxidant effect is significantly reduced, the contents of TC, TG, and LDL-C are significantly increased, the content of HDL-C is reduced, the body weight is significantly increased, and the liver index is significantly increased. *Lactobacillus bulgaricus*, a facultative anaerobe, can ferment glucose, fructose and lactose, but cannot utilize sucrose. *Streptococcus thermophilus*, the facultative anaerobic, ferments lactose, and does not ferment inulin and mannitol. *Bifidobacterium longum*, the facultative anaerobic, can utilize lactose, ribose, raffinose, xylose, mannose, fructose, galactose, sucrose, maltose, melibiose, and the like. *Streptococcus thermophilus, Bifidobacterium longum* and *Lactobacillus bulgaricus* are mixed for fermentation culture, which is better than separate fermentation culture, because *Lactobacillus bulgaricus* and *Bifidobacterium longum* are decomposed to provide lactic acid, amino acids and the like, which provide nutrients for the growth of *Streptococcus thermophilus*, and formic acid, short-chain fatty acids, folic acid and the like produced by *Streptococcus* thermophile, can promote the growth of the *Lactobacillus bulgaricus* and the *Bifidobacterium longum*; in the initial fermentation stage of the *Streptococcus thermophilus*, the acid production is fast, when the pH is reduced to about 6.2-6.7, the *Bifidobacterium longum* is promoted to proliferate in a large amount, and a large amount of small molecular acid is further produced; when the pH is continuously reduced to about 4, the *Lactobacillus bulgaricus* proliferates in a large amount, and a large number of lactic acid and amino acid are produced; on the contrary, the growth of the *streptococcus acidophilus* and the *Bifidobacterium longum* is promoted, and the three complement each other and promote each other, so that the good effect of degrading crude polysaccharide can be achieved. In addition, the fermentation and extraction under the low-oxygen condition are beneficial to the proliferation and growth of facultative anaerobes, and can effectively prevent the oxidation of substances under the low-oxygen condition at the same time, so that the generated bioactive substances can exert better effects.

The comparative example 10 is compared with the embodiment 3, the step S7 phosphorylation is not performed, the solubility of the *Auricularia auricula* polysaccharide prepared is significantly reduced, the antioxidant effect is significantly reduced, the contents of TC, TG, and LDL-C are significantly increased, the content of HDL-C is reduced, the body weight is significantly increased, and the liver index is significantly increased. The biological activity of polysaccharides depends on the molecular properties of the polymer, including the molecular weight of monosaccharides, the conformation of polysaccharide chains, the degree of polymerization of branched chains, and the type of glycosidic bonds. According to that present invention, the fermented *Auricularia auricula* polysaccharide is subject to phosphorylation modification, and the structure is changed after the chemical group substitutes the hydroxyl group on the polysaccharide, so that more hydroxyl groups are exposed, the antioxidant activity is enhanced, and the anti-inflammatory, anti-aging, hypoglycemic and other effects of the polysaccharide are improved; and meanwhile, the solubility of the polysaccharide is further improved, such that the polysaccharide is more easily absorbed.

The comparative example 11 is compared with the embodiment 3, the step S8 deproteinization is not performed, the solubility of the prepared *Auricularia auricula* polysaccharide is reduced, and the extraction rate is reduced.

The polysaccharide obtained after protein removal has higher purity, higher solubility and higher activity.

The comparative example 12 is compared with the embodiment 3, the step S10 zinc chelating is not performed, the antioxidant effect of the *Auricularia auricula* polysaccharide prepared is significantly reduced, the contents of TC, TG, and LDL-C are significantly increased, the content of HDL-C is reduced, the body weight is significantly increased, and the liver index is significantly increased. The refined *Auricularia auricula* polysaccharide after deproteinization and decolorization further reacts with zinc salt, chelating groups such as the hydroxyl group and the like on the surface coordinate with Zn ions through complexation to form a stable polysaccharide-zinc compound, and the polysaccharide-zinc compound has the effects of reducing blood fat, regulating total cholesterol and effectively improving HDL cholesterol.

The above description is only a preferred embodiment of the present invention, and is not intended to limit the present invention, any modification, equivalent substitution, improvement, and the like within the spirit and principle of the present invention shall be included in the protection scope of the invention.

What is claimed is:

1. A preparation method of *Auricularia auricula* polysaccharide, comprising the steps of:

S1) drying and crushing *Auricularia auricula*, and then degreasing the *Auricularia auricula* by a supercritical fluid extraction process to obtain a degreased *Auricularia auricula;* wherein in S1, conditions of the supercritical fluid extraction process are as follows: a flow rate of $CO_2$ is in a range of 7-12 L/h, a pressure is in a range of 12-25 MPa, a temperature is in a range of 45-60° C., and an extraction time is in a range of 1-2 h;

S2) adding the degreased *Auricularia auricula* obtained in S1 into water, adding snailase, performing preliminary enzymolysis, deactivating the snailase, concentrating and drying an obtained system to obtain a preliminary enzymolysis product;

S3) adding the preliminary enzymolysis product prepared in S2 into a $H_2O_2$ solution, carrying out ultrasonic treatment, adding sodium bisulfite thereto, carrying out alcohol precipitation, centrifuging and drying to obtain an *Auricularia auricula* raw sugar extract;

S4) dissolving the *Auricularia auricula* raw sugar extract prepared in S3 in water, adding a complex enzyme thereto, conducting the secondar enzymolysis, and deactivating the complex enzyme to obtain a secondary enzymolysis extract, wherein the complex enzyme is at least one selected from the group consisting of β-glucanase, saccharifying enzyme, cellulase, pectinase, α-amylase, and α-glucosidase;

S5) respectively streaking *Lactobacillus bulgaricus, Streptococcus thermophilus* and *Bifidobacterium longum* in a Gauze's medium, and carrying out activation culture to obtain a strain seed liquid;

S6) inoculating the strain seed liquid prepared in S5 into the secondary enzymolysis extract prepared in S4, and carrying out fermentation culture, followed by concentration, alcohol precipitation and centrifugation to obtain a fermented *Auricularia auricula* polysaccharide;

S7) adding the fermented *Auricularia auricula* polysaccharide prepared in S6 into water, adding sodium sulfate and a phosphorylation reagent thereto, adjusting a pH value of an obtained mixture to 8.8-9.2, heating and subjecting the resulting mixture to reaction, dialyzing, and concentrating to obtain a phosphorylated *Auricularia auricula* polysaccharide solution;

S8) adding the phosphorylated *Auricularia auricula* polysaccharide solution obtained in S7 into a Sevag reagent, subjecting the resultant mixture to reaction under stirring, centrifuging to deproteinize the phosphorylated *Auricularia auricula* polysaccharide solution, repeating the preceding deproteinization steps on the resulting liquid 1-3 times and removing the remaining Sevag reagent therein under reduced pressure to obtain a deproteinized *Auricularia auricula* polysaccharide;

S9) adding activated carbon and the deproteinized *Auricularia auricula* polysaccharide prepared in S8 into water, performing adsorption under stirring, filtering, performing alcohol precipitation on the resulting liquid, and centrifuging to obtain a refined *Auricularia auricula* polysaccharide;

S10) dissolving the refined *Auricularia auricula* polysaccharide prepared in S9 and trisodium citrate in water, adding a zinc salt, adjusting a pH value of the resulting solution to 7.2-7.5, heating and subjecting the resulted mixture to reaction under stirring, filtering, performing alcohol precipitation on the resulting liquid, centrifuging, collecting the resulting solid, and freeze-drying the resulting solid collected to obtain the *Auricularia auricula* polysaccharide.

2. The preparation method according to claim 1, wherein in S2, a mass ratio of the degreased *Auricularia auricula* to the snailase is in a range of 100:5 to 100:3, and the preliminary enzymolysis is performed at a temperature of 40-50° C. for 1-2 h;

in S3, a concentration of $H_2O_2$ in the $H_2O_2$ solution is in a range of 2-5 wt %; and the ultrasonic treatment is performed at a power of 1500-2000 W for 30-50 minutes; and in S4, the complex enzyme is at least two selected from the group consisting of β-glucanase, saccharifying enzyme, cellulase, pectinase, α-amylase, and α-glucosidase; a mass ratio of the *Auricularia auricula* raw sugar extract to the complex enzyme is in a range of 100:7 to 100:5, and the secondary enzymolysis is performed at a temperature of 40-45° C. for 3-5 hours.

3. The preparation method according to claim 2, wherein the complex enzyme is a compound mixture of the β-glucanase and the α-glucosidase at a mass ratio of 3:1 to 5:1.

4. The preparation method according to claim 1, wherein in S5, conditions of the activation culture are as follows: under a low-oxygen condition, a temperature of 40-45° C., a time of 18-24 hours, and a bacteria content of the strain seed liquid being $10^8$-$10^9$ cfu/mL; and in S6, inoculum sizes of the *Lactobacillus bulgaricus*, the *Streptococcus thermophilus* and the *Bifidobacterium longum* are respectively 3-5%, 1-3% and 1-2%, respectively; the fermentation culture is performed under conditions: the low-oxygen condition, a temperature of 40-45° C., and a time of 36-48 h;

wherein the low-oxygen condition is as follows: a content of $O_2$ is in a range of 5 to 7%, a content of $CO_2$ is in a range of 5 to 10%, and the remaining amount is nitrogen, where % is a volume percentage content.

5. The preparation method according to claim 1, wherein in S7, the phosphorylation reagent is at least two selected from the group consisting of polyphosphoric acid, sodium tripolyphosphate, sodium trimetaphosphate, pyrophosphoric acid, and phosphorus pentoxide; a mass ratio of the fermented *Auricularia auricula* polysaccharide, the sodium sulfate, the phosphorylation reagent, and the water is in a range of 10: 30-50:2-4: 100; the resulting mixture is heated and subjected to reaction at a temperature of 70-90° C. for 3-5 hours, a dialysis bag used for the dialyzing has a pore size of 5000-15000 Da, and the dialyzing is performed for 24-48 hours;

in S8, a mass ratio of the phosphorylated *Auricularia auricula* polysaccharide solution to the Sevage reagent is in a range of 1:7 to 1:3; and the reaction under stirring is performed for 20-30 minutes;

in S9, a mass ratio of the deproteinized *Auricularia auricula* polysaccharide to the activated carbon is in a range of 100:15 to 100:12; and the adsorption under stirring is performed for 30-50 minutes; and in S10, a mass ratio of the refined *Auricularia auricula* polysaccharide, the trisodium citrate, the zinc salt is in a range of 100: 5-12:22-27; the resulted mixture is heated and subjected to reaction at a temperature of 45-55° C. for 1-2 h, under stirring at a stirring speed of 300-500 r/min; and the zinc salt is at least one selected from the group consisting of zinc chloride, zinc sulfate, and zinc nitrate.

6. The preparation method according to claim 5, wherein the phosphorylation reagent is a mixture of the sodium tripolyphosphate, the sodium trimetaphosphate, and the pyrophosphoric acid at a mass ratio of 3-7:2:0.2-0.4.

7. The preparation method comprising the following steps:

S1) drying and crushing the *Auricularia auricula*, and then degreasing the *Auricularia auricula* by the supercritical fluid extraction process to obtain the degreased *Auricularia auricula;*

S2) adding 100 parts by weight of the degreased *Auricularia auricula* in S1 into 200 parts by weight of water, adding 3-5 parts by weight of the snailase, carrying out the preliminary enzymolysis at 40-50° C. for 1-2 hours, deactivating the snailase at 100-110° C. for 10-15 minutes, concentrating the resulting preliminary enzymolysis mixture with an organic membrane to ⅓-¼ of an original volume of the resulting preliminary enzymolysis mixture, and drying to obtain the preliminary enzymolysis product;

S3) adding 100 parts by weight of the preliminary enzymolysis product prepared in S2 into 100 parts by weight of 2-5 wt % $H_2O_2$ solution, carrying out ultrasonic treatment for 30-50 minutes at 1500-2000 W, adding 7-12 parts by weight of sodium bisulfite thereto, carrying out alcohol precipitation, centrifuging and drying to obtain the *Auricularia auricula* raw sugar extract;

S4) dissolving 100 parts by weight of the *Auricularia auricula* raw sugar extract prepared in S3 in 100 parts by weight of water, adding 5-7 parts by mass of the complex enzyme, carrying out the secondary enzymolysis at 40-45° C. for 3-5 hours, and deactivating the complex enzyme at 100-110° C. for 10-15 minutes to obtain the secondary enzymolysis extract; wherein the complex enzyme is a compound mixture of β-glucanase and α-glucosidase at a mass ratio of 3:1 to 5:1;

S5) respectively streaking the *Lactobacillus bulgaricus*, the *Streptococcus thermophilus*, and the *Bifidobacterium longum* in the Gauze's medium, performing activation culture at 40-45° C. for 18-24 hours under a low-oxygen condition to obtain the strain seed liquid with a bacteria content of $10^8$-$10^9$ cfu/mL;

S6) inoculating the strain seed liquid prepared in S5 into the secondary enzymolysis extract prepared in S4, wherein inoculum sizes of the *Lactobacillus bulgaricus*, the *Streptococcus thermophilus*, and the *Bifidobacterium longum* are respectively 3-5%, 1-3%, and 1-2%, respectively, conducting fermentation culture at 40-45° C. for 36-48 hours under the low-oxygen condition, concentrating, performing alcohol precipitation, and centrifuging to obtain the fermented *Auricularia auricula* polysaccharide; wherein the low-oxygen condition is as follows: a content of $O_2$ is in a range of 5% to 7%, a content of $CO_2$ is in a range of 5% to 10%, and a balance is nitrogen, where % is a volume percentage content;

S7) adding 10 parts by weight of the fermented *Auricularia auricula* polysaccharide prepared in S6 into 100 parts by weight of water, adding 30-50 parts by weight of the sodium sulfate and 2-4 parts by weight of the phosphorylation reagent, adjusting the pH value of the obtained mixture to 8.8-9.2, heating and subjecting the resulting mixture to reaction at 70-90° C. for 3-5 hours, dialyzing for 24-48 hours by using a dialysis bag with a pore size of 5000-15000 Da, concentrating the resulting phosphorylation mixture with an organic membrane to ⅓-¼ of an original volume of the resulting phosphorylation mixture to obtain the phosphorylated *Auricularia auricula* polysaccharide solution; wherein the phosphorylation reagent is a mixture of sodium tripolyphosphate, sodium trimetaphosphate and pyrophosphoric acid with a mass ratio of 3-7:2:0.2-0.4;

S8) adding 10 parts by weight of the phosphorylated *Auricularia auricula* polysaccharide solution obtained in S7 into 30-70 parts by weight of the Sevag reagent, subjecting the resultant mixture to reaction under stirring for 20-30 min and centrifuging to deproteinize the phosphorylated *Auricularia auricula* polysaccharide solution, repeating preceding deproteinization steps on the resulting liquid for 1-3 times, merging resulting liquids, and removing the solvent therein under reduced pressure to obtain the deproteinized *Auricularia auricula* polysaccharide;

S9) adding 12-15 parts by weight of the activated carbon and 100 parts by weight of the deproteinized *Auricularia auricula* polysaccharide prepared in S8 into 200 parts by weight of water, performing adsorption under stirring for 30-50 minutes, filtering, performing alcohol precipitation on the resulted liquid, and centrifuging to obtain the refined *Auricularia auricula* polysaccharide;

S10) dissolving 100 parts by weight of the refined *Auricularia auricula* polysaccharide prepared in S9 and 5-12 parts by weight of the trisodium citrate in 200 parts by weight of water, adding 22-27 parts by weight of the zinc salt, adjusting the pH value of the resulting solution to 7.2-7.5, heating the resulted mixture to 45-55° C. and subjecting the resulted mixture to reaction under stirring at 300-500 r/min for 1-2 h, filtering, performing alcohol precipitation on the resultant liquid, centrifuging, collecting the resulting solid, and freeze-drying the resulting solid collected to obtain the *Auricularia auricula* polysaccharide; wherein the alcohol precipitation comprises: adding absolute ethyl alcohol to the resultant liquid until an ethanol content in a resulting system is 75-85%, and subjecting the resulting system to precipitation for 12-24 hours.

8. A method for reducing blood fat, comprising:

administrating the *Auricularia auricula* polysaccharide prepared by the preparation method according to claim 1 to a subject in need thereof.

9. A method for regulating a total cholesterol, comprising:

administrating the *Auricularia auricula* polysaccharide prepared by the preparation method according to claim 1 to a subject in need thereof.

10. A method for improving high density lipoprotein (HDL) cholesterol, comprising:

administrating the *Auricularia auricula* polysaccharide prepared by the preparation method according to claim 1 to a subject in need thereof.

11. A method for reducing blood sugar, comprising:

administrating the *Auricularia auricula* polysaccharide prepared by the preparation method according to claim 1 to a subject in need thereof.

12. A method for resisting inflammation, comprising:

administrating the *Auricularia auricula* polysaccharide prepared by the preparation method according to claim 1 to a subject in need thereof.

* * * * *